United States Patent [19]

Heyman

[11] Patent Number: 5,237,516
[45] Date of Patent: Aug. 17, 1993

[54] METHOD OF RECERTIFYING A LOADED BEARING MEMBER USING A PHASE POINT

[75] Inventor: Joseph S. Heyman, Williamsburg, Va.

[73] Assignee: The United States of America as represented by the United States National Aeronautics and Space Administration, Washington, D.C.

[21] Appl. No.: 720,153

[22] Filed: Jun. 19, 1991

[51] Int. Cl.[5] .................... G01H 1/00; G01N 29/16
[52] U.S. Cl. .................................. 364/508; 73/761; 73/862.59; 364/571.03
[58] Field of Search ............ 364/506, 508, 571.01, 364/571.03, 579, 580; 73/761, 862.59, 581, 1 B, 657

[56] References Cited

U.S. PATENT DOCUMENTS 3,822,587  7/1974  Makino et al. .................... 73/761
4,363,242 12/1982  Heyman .............................. 73/761

Primary Examiner—Thomas G. Black
Assistant Examiner—Michael Zanelli
Attorney, Agent, or Firm—Kevin B. Osborne

[57] ABSTRACT

A method of recertifying a load on a bearing member using a pulsed phase locked loop (P2L2) system. A first tone burst signal with a corresponding first phase signal is generated in the bearing member in a first load condition. The sample/hold of the P2L2 is adjusted to a determined phase point on the first phase signal and then the P2L2 is locked at this phase period to determine a first load measurement. Next, the phase sample point is correlated with a corresponding position w on the first tone burst signal. A second tone burst with a corresponding second phase signal is then generated at some later time in the bearing member in a second load condition. The sample/hold is adjusted to the same sample/hold phase point as before and then the output frequency of the P2L2 is adjusted until the sample/hold is positioned at the previously determined phase point corresponding to position w on the second tone burst signal. The P2L2 is then locked at this phase point to determine a frequency indicative of the load of the second loading condition.

2 Claims, 7 Drawing Sheets

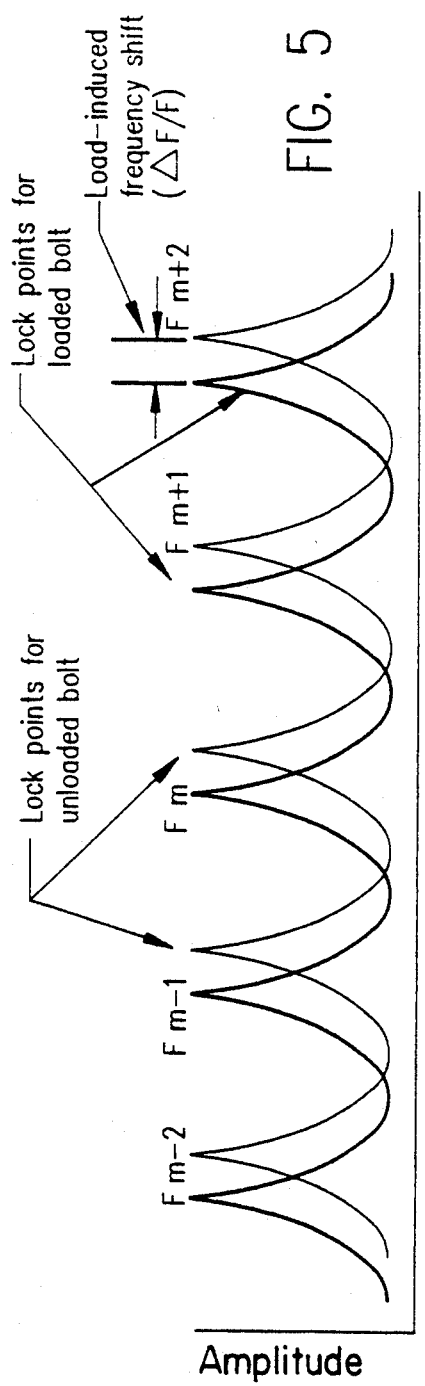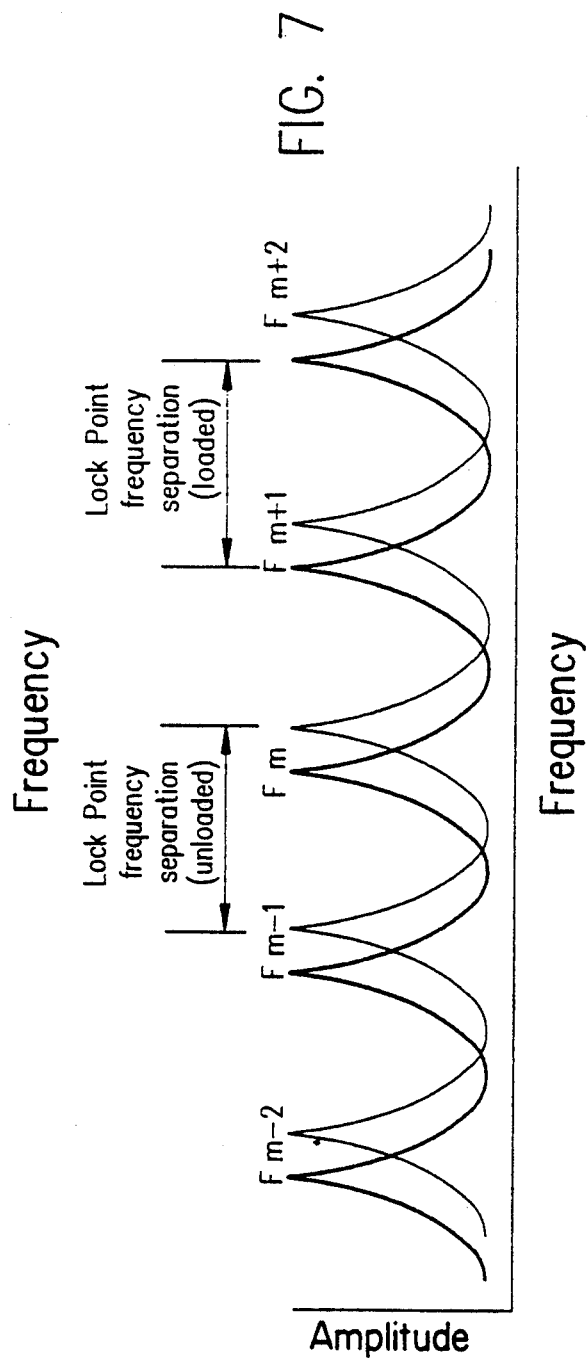

METHOD OF RECERTIFYING A LOADED BEARING MEMBER USING A PHASE POINT

ORIGIN OF THE INVENTION

The invention described herein was made by an employee of the United States Government and may be manufactured and used by and for the Government for governmental purposes without the payment of any royalties thereon or therefor.

CROSS-REFERENCE

This application is related to a co-pending application entitled "Method of Recertifying a Loaded Bearing Member", Ser. No. 07/717,755, filed Jun. 19, 1991 and issued as U.S. Pat. No. 5,150,620 on Sep. 29, 1992.

BACKGROUND OF THE INVENTION

1. Technical Field

The present invention relates generally to material testing and more particularly to a method of recertifying the load on a bearing member via ultrasound techniques.

2. Discussion of the Related Art

The pulsed phase locked loop strain monitor, or P2L2, is a device which can be utilized to nondestructively measure the load in a bearing member such as a bolt, connector, etc. The P2L2, described in U.S. Pat. No. 4,363,242 to Heyman, measures acoustic phase changes and displays frequency changes which are indicative of changes in the load of the bearing member. By only determining load changes, the P2L2 requires that the ultrasonic sensor be kept on the bearing member during tightening or other load applications. Measurement of the load in a tightened bearing member, i.e., load recertification, is not possible because temperature variations as well as substitutions of various P2L2 elements such as transducers, cables, ultrasonic bonding, coupling, the P2L2 member itself, etc. are not corrected for a subsequent, after load measurement. In addition, it is often difficult to return to the same frequency point to correctly determine a subsequent frequency shift, thereby resulting in incorrect load determination.

Other non-destructive load testing systems include using an ultrasonic monitor to measure the time of flight of ultrasonic waves through a bolt. This measured time of flight is indicative of bolt loading. Such time of flight systems are harder to use and generally less accurate than P2L2 systems because the correct threshold trigger point must be selected to give the correct load measurement. In addition, load recertification of an already tightened bearing member is difficult for the reasons discussed above in connection with the P2L2 system.

OBJECTS OF THE INVENTION

It is accordingly an object of the present invention to permit load recertification of a loaded bearing member.

It is another object of the present invention to accomplish the foregoing object while accounting for changes in temperature.

It is a further object of the present invention to accomplish the foregoing objects while permitting substitutions of various P2L2 system components and recertification subsystem components.

It is another object of the present invention to avoid the difficulties and incorrect load determination associated with returning to a frequency peak lock point number after a period of time has elapsed.

It is yet another object of the present invention to accomplish the foregoing objects non-destructively.

It is a further object of the present invention to accomplish the foregoing objects in a simple manner.

Additional objects and advantages of the present invention are apparent from the drawings and specification.

SUMMARY OF THE INVENTION

The foregoing and additional objects are obtained by a method of recertifying a load on a bearing member according to the present invention. The method uses a pulsed phase locked loop (P2L2) system comprising a voltage controlled oscillator having an output frequency controlling an ultrasonic transducer coupled to the bearing member, a phase detector which compares the phase of an ultrasonic tone burst applied to the bearing member via the transducer to the phase of a tone burst reflected through the bearing member, and an adjustable sample/hold for selecting a phase point of the reflected tone burst, wherein the P2L2 system can be locked such that the phase is constant and the output frequency of the voltage controlled oscillator changes as the bearing member is loaded. The recertification method comprises the steps of:

(1) generating a first tone burst signal and a corresponding first phase signal in the bearing member in a first load condition;

(2) adjusting the sample/hold to a determined phase point on the first phase signal;

(3) locking the P2L2 on the first phase signal at the sample/hold phase point to determine a first load measurement;

(4) correlating the sample/hold phase point with a corresponding position w on the first tone burst signal;

(5) generating a second tone burst signal and a corresponding second phase signal in the bearing member in a second load condition;

(6) adjusting the sample/hold setting to the same sample/hold phase point of step (3);

(7) adjusting the output frequency of the voltage controlled oscillator until the sample/hold is positioned at the previously determined phase point corresponding to position w on the second tone burst signal; and (8) locking the P2L2 at this phase point corresponding to position w on the second tone burst signal to determine a frequency of the tone burst which is indicative of the second loading condition.

BRIEF DESCRIPTION OF THE DRAWINGS

FIG. 5 is a graph schematically depicting a typical ultrasonic frequency spectrum of a bearing member showing the lock point for a loaded and unloaded bolt and the load-induced frequency shift of a typical lock point;

FIG. 7 is a graph depicting the frequency spacing of successive lock points for a loaded and unloaded bolt;

DETAILED DESCRIPTION OF THE PREFERRED EMBODIMENT

Figure 1:
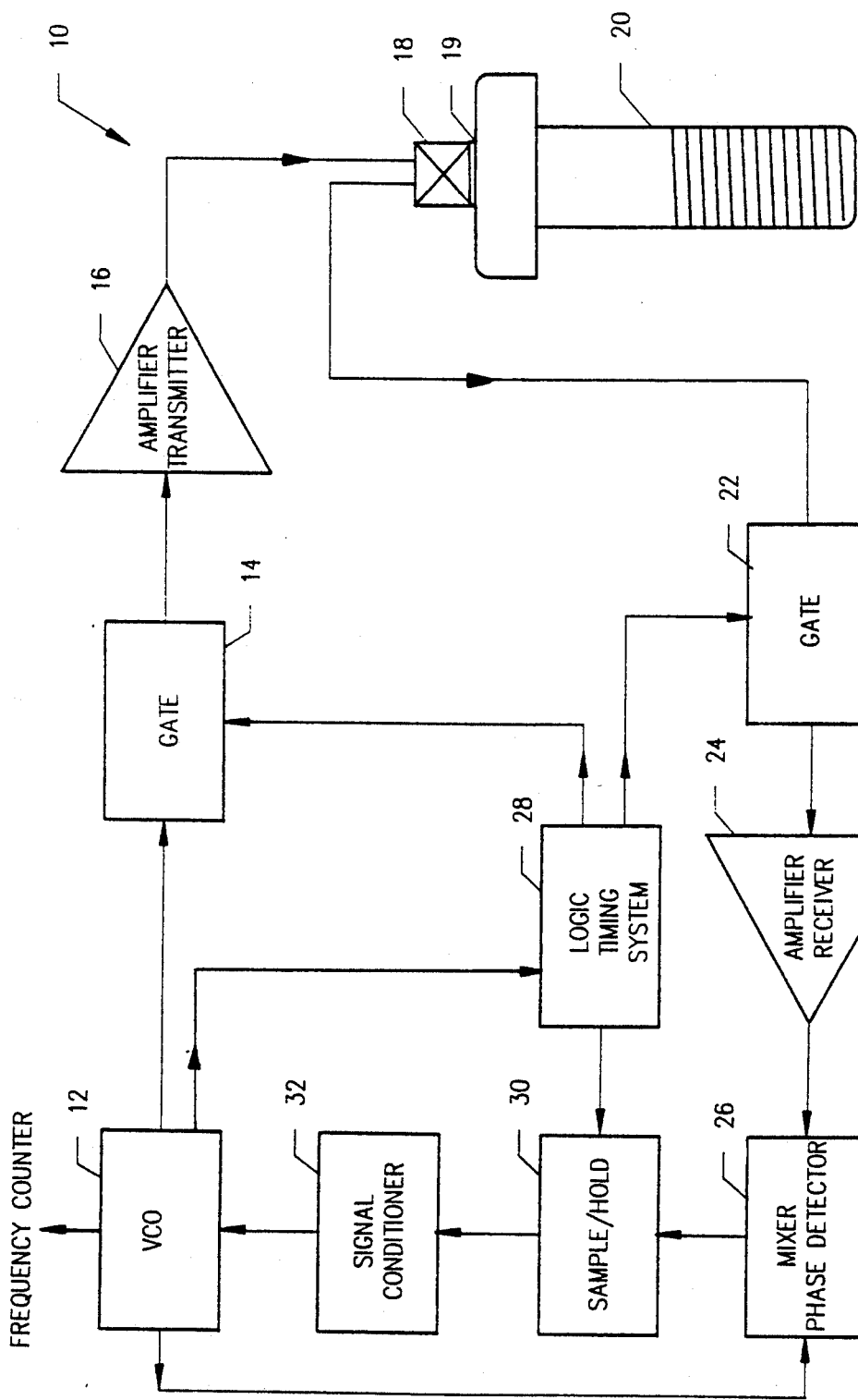
FIG. 1 is a schematic diagram of the constituent elements of a prior art pulsed phase locked loop strain monitor.

Referring to FIG. 1, a pulse phase locked loop strain monitor or P2L2 10 is schematically shown. The P2L2 is described in greater detail in U.S. Pat. No. 4,363,242 to Heyman, the specification of which is hereby incorporated by reference. The P2L2 measures acoustic phase change and reads out corresponding frequency changes. In general terms, the RF output of a voltage controlled oscillator (VCO) 12 is periodically gated by gate 14 and then amplified and transmitted via amplifier transmitter 16 to an ultrasonic transducer 18. Transducer 18 is affixed to an end of test material 20 via an appropriate couplant 19 such as water, glycerin, light machine oil, etc. and produces an acoustic tone burst or sound wave pulse which propagates in bearing member 20. The produced acoustic signal may have any ultrasonic frequency near the center of the operating frequency bandwidth of the compound resonator formed by the transducer bonded to the load bearing member. Also, test material 20 may be a load bearing member such as a bolt or other load bearing coupling of any geometrical configuration.

The generated tone burst or sound wave pulse is reflected by the far end of test material 20 back to transducer 18 and converted to an electrical signal by the transducer. The signal is gated by gate 22, amplified by amplifier receiver 24, and sent to mixer phase detector 26. Mixer phase detector 26 also receives the output of VCO 12 and produces a DC signal proportional to the phase difference between these two inputs. Logic timing system 28 controls the gating time of gates 14 and 22 in response to a signal received from VCO 12. Logic timing system 28 also controls the time at which a phase point of the phase difference signal is sampled and held by sample/hold circuit 30. This sampled signal is then appropriately conditioned by signal conditioner 32 and sent to VCO 12 to control the VCO output frequency. The P2L2 locks onto resonant frequencies which correspond to quadrature which represents a phase delay of $2\pi N + \phi_o$, where N is an integer and $\phi_o$ is typically 90°.

Once the frequency F is locked at a particular lock point, any deviation in the propagation length or sound velocity of the test material 20 results in a frequency change $\Delta F$ needed to maintain a fixed phase condition. Thus, the P2L2 10 measures frequency changes to indicate load changes, i.e., tension or compression, which change the sound velocity and propagation length. This frequency change relationship ($\Delta F/F$) resulting from the load change is interpreted via a load-member-specific ultrasonic load calibration factor Cl, which is defined in units of lb/ppm to indicate pounds of load change per parts per million of normalized frequency shift. The factor Cl is determined by obtaining various frequency changes with known loads for the particular bearing member and obtaining a polynomial function which represents an acceptable curve fit for the obtained data. For simplicity, a first order linear polynomial is generated and the x-coefficient representing the slope of the curve is expressed as Cl. Then when the load is changed, the normalized frequency shift is multiplied by the Cl factor to determine the load change. See FIG. 4.

If the load is the only parameter changed, then the displayed frequency change is indicative solely of this load change. However, changes in other parameters such as equipment and temperature may also affect the frequency changes, thereby contaminating the subsequent load change determination. Compensation must accordingly be made for these other parameter changes. Changes in the measurement equipment configuration typically occur over the period of time between the initial and subsequent measurements as specific components are replaced due to loss, failure or interchangement with other configurations. Also, temperature fluctuations can have significant effects; e.g., a 1° F. change can result in a frequency change which would incorrectly indicate a 350 lb. load change in a shuttle wheel bolt.

Figure 2:
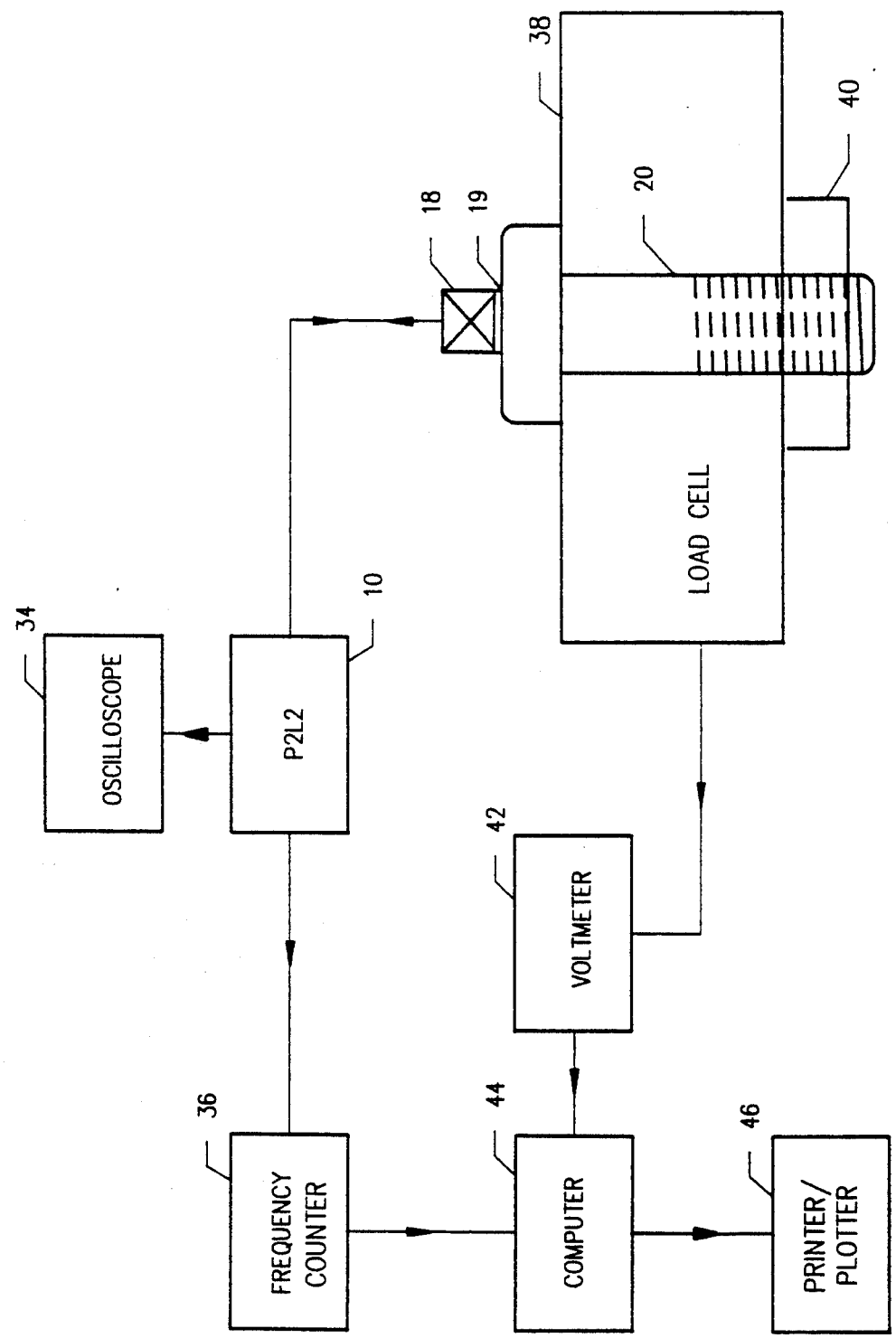
FIG. 2 is a schematic diagram of a prior art pulsed phase locked loop strain monitor and associated hardware.

As shown in FIG. 2, an oscilloscope 34 and a frequency counter 36 are connected to P2L2 10 to provide a respective visual display and an electronic readout of the VCO 12 frequency (FIG. 1). Test material 20, e.g., a bolt, is passed through a load cell 38 and has a nut 40 threaded on the end opposite transducer 18 which is tightened to induce a load. Alternatively, the transducer can be coupled to the nut end of the bolt. Load cell 38 duplicates the actual field thickness where the bolt is to be installed. A voltmeter 42 reads the voltage induced in load cell 38 by the tightening of nut 40. Alternatively, the load can be measured by a hydraulic or other type of indicator. The outputs of voltmeter 42 and frequency counter 36 are read by computer 44 as nut 40 is tightened. This data is fed to an appropriate printer/plotter 46 for display.

Figure 3:
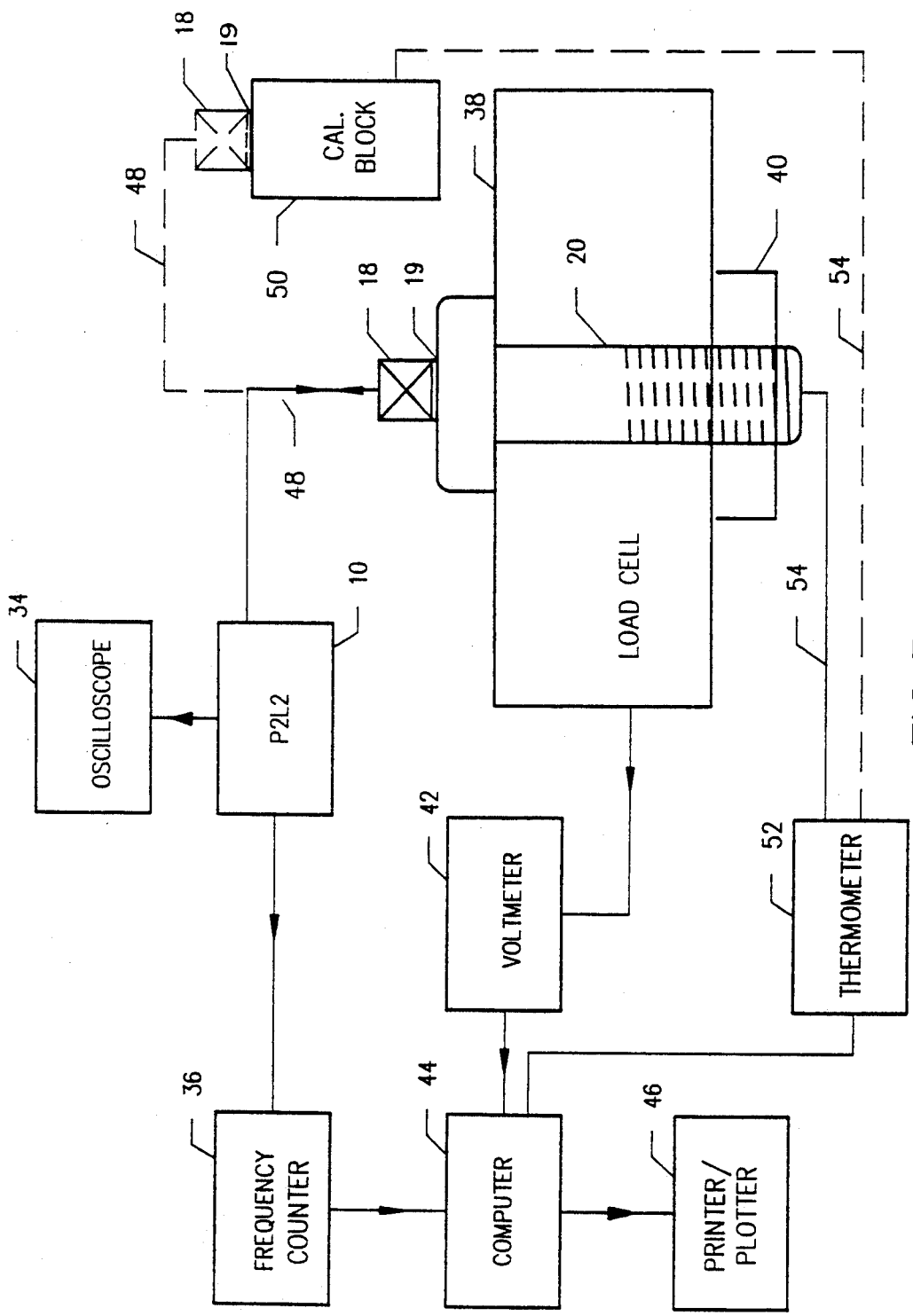
FIG. 3 is a schematic diagram of a pulsed phase locked loop equipment configuration according to the present invention.
Figure 4:
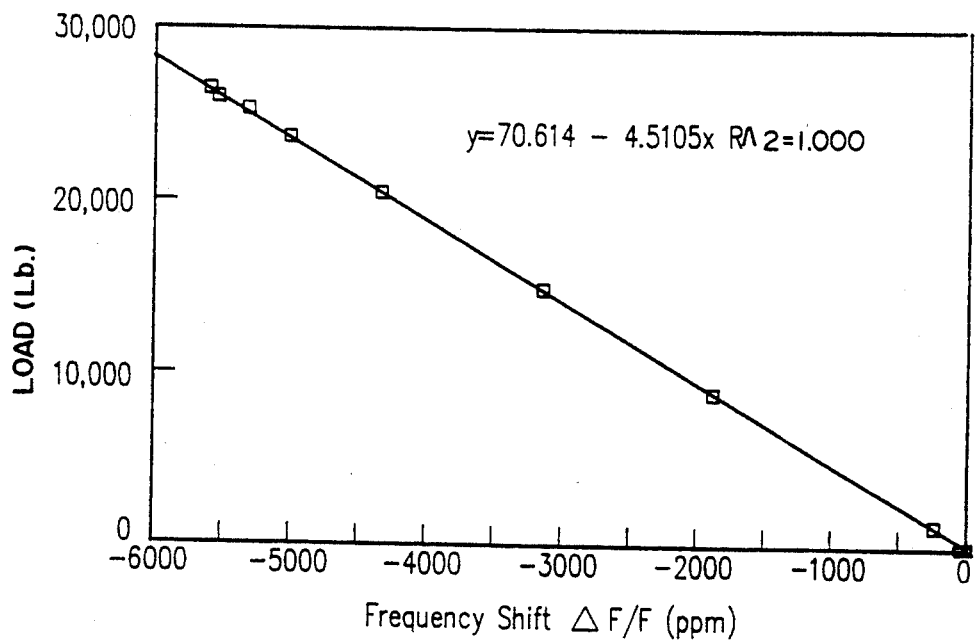
FIG. 4 is a graph showing the correlation of the frequency shift $\Delta F/F$ with bolt load.

The method and system for testing load bearing members according to the present invention will now be described with particular reference to FIGS. 3 and 4. Prior to performing any load measurement of bearing member 20, the particular equipment configurations, e.g., P2L2 10, transducer 18, connecting cable 48, couplant 19, etc., for detecting the VCO frequency changes is selected. This configuration, designated configuration A, is connected to reference or calibration block 50 as indicated by the dotted line indicating cable 48 in FIG. 3. In addition, a thermometer 52 is connected to reference block 50 via cable 54, as indicated by the dotted line 54 in FIG. 3. Of course, the thermometer may be hand-held and read. The following standard measurements and determinations are obtained for reference block 50:

(1) measuring the standard lock point frequency F1 (Hz) via the particular transducer 18, cable 48, couplant, and P2L2 10 of configuration A;

(2) measuring the temperature T1 (°F.) via thermometer 52 and cable 54;

(3) determining the calibration standard lock point number s; and (4) determining the reference block ultrasonic thermal calibration factor Ctr (ppm/°F.).

Step (3) involves measuring the frequency separation or spacing between two successive lock points at temperature T1 and then dividing F1 by this measured spacing. Each lock point is a mechanical resonant frequency of the calibration block 50. In FIG. 5 the general case is illustrated wherein the lock point number is represented by m and the mechanical resonant frequencies are represented by peaks. The fundamental resonant frequency corresponds to m=1 and the mth harmonic resonant frequency is represented by the mth peak in FIG. 5. The value of m is generally equal to $F(F_{m+1}-F_m)$, and s is specifically equal to $F1(F_{s+1}-F_s)$, wherein $F_s$ and $F_{s+1}$ are any two successive harmonic frequencies. The determination of the lock point number m or s allows the P2L2 to return to the same frequency peak after an induced load to determine the true load-induced frequency shift. The same lock point number must be used because often this frequency shift is greater than the harmonic interval and accordingly merely using the frequency F1 to recertify the load could result in a significant misreading of the frequency change. The lock point number is optimally chosen so that the frequencies lie near the center of the operating frequency bandwidth of the compound resonator formed by the transducer 18 bonded to the load bearing member 20 by the couplant 19.

Figure 6:
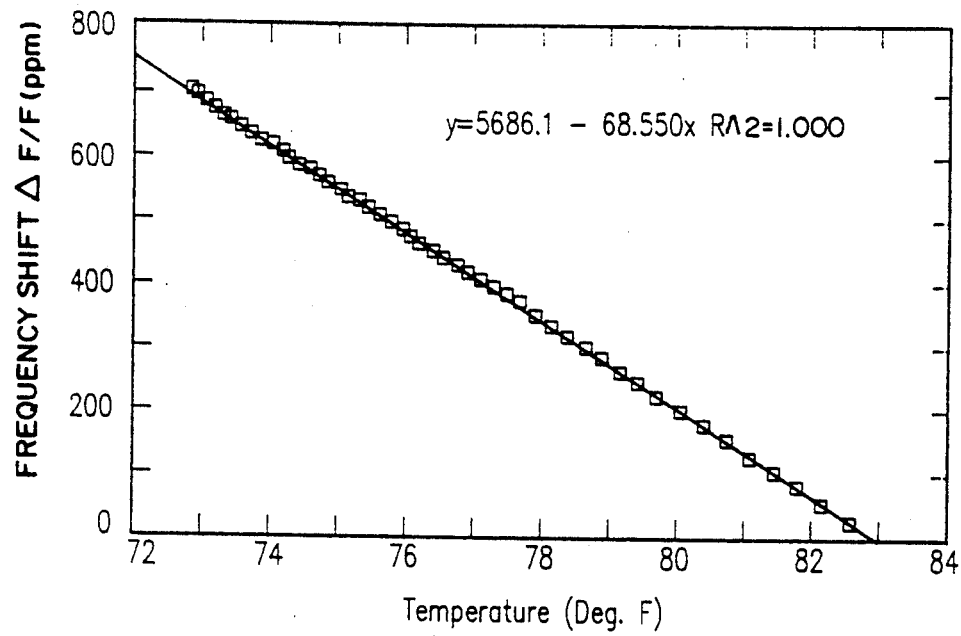
FIG. 6 is a graph showing the correlation of the frequency shift with temperature.

The determination of the material and geometrical specific Ctr in step (4) involves use of an experimentally derived relationship between the change in resonant frequency and harmonics, i.e., a shift in the lock point s and the change in temperature, as generally represented in FIG. 6. For example, the reference block may be placed in an oven and its frequency change observed at various temperatures. Like Cl, Ctr represents the slope of a linear or other polynomial function which best fits the generated data curve.

Next, another equipment configuration comprising at least one element, and as many as all elements, different from the corresponding elements in configuration A is selected for determining the VCO frequency changes. This other configuration, designated configuration B, is also connected to reference block 50 as indicated by the dotted lines in FIG. 3 prior to performing any load measurement of bearing member 20. If any element is changed in the configuration, the true propagation path length also changes, resulting in all of the lock point frequencies being shifted by approximately the same amount. Similarly, a temperature change can also shift the lock point frequencies. Equipment offset errors are obtained for configuration B by the following steps:

(5) measuring the reference block lock point frequency F1a (Hz) via the particular transducer 18, cable 48, couplant and P2L2 10 of configuration B using lock point number s;

(6) measuring the reference block temperature T1a (°F.) via thermometer 52 and cable 54;

(7) compensating F1a for temperature difference T1−T1a using Ctr such that $$F1aC = F1a - Ctr(T1 - T1a)F1/1000000,$$

wherein F1aC is compensated F1a; and (8) determining the dimensionless offset compensation factor Fo1 expressed in parts of frequency shift per million parts of operating frequency:

$$Fo1 = ((F1 - F1aC)/F1)1000000,$$

to allow compensation for the difference in resonant frequencies determined from using two different equipment configurations. If no compensation is made for the temperature-induced frequency change, F1a is substituted for F1aC in the preceding equations.

Still using equipment configuration B, the transducer 18 and thermometer 52 are then connected to bearing member 20 and the following measurements obtained:

(9) measuring the reference lock point frequency F2 (Hz) of the unloaded bolt (bearing member 20) via the particular transducer 18, cable 48, couplant and P2L2 10 of configuration B;

(10) measuring the unloaded bolt reference temperature T2 (°F.) via thermometer 52 and cable 54;

(11) determining the bolt lock point number b by measuring the frequency separation or spacing between two lock points and dividing this spacing into F2 as described above in reference to lock point number s;

(12) compensating the unloaded bolt reference frequency for equipment offset errors with the previously determined reference block offset compensation factor Fo1 (step 8) by $$F2C = F2 + F2(Fo1)/1000000,$$

wherein F2C is the compensated frequency;

(13) determining the bolt ultrasonic load calibration factor Cl (lb/ppm) as discussed above; and

(14) determining the material and geometric specific, unloaded bolt ultrasonic thermal calibration factor Ct (ppm/°F.) using the experimentally derived relationship between the lock point number b and the change in temperature as generally shown in FIG. 6 to compensate for any subsequent temperature deviation from the initial bolt temperature T2. Ct may be determined by the same method as Ctr.

Once all of the measurements and determinations are made in steps (1)–(14), the bearing member 20, e.g., a bolt, is installed under load (preloaded) in a field condition rather than in the approximating load cell 38. In all likelihood, the tester would prefer the widest possible latitude in selecting the particular equipment configuration to determine the load indicating VCO frequency changes at the particular test time due to equipment repair, replacement and availability. A new configuration C having at least one element and possibly all elements, different from the corresponding elements in configurations A and B, is selected. Also, the effects of a different temperature at test time from the initial measurements must be taken into account. As stated previously, it is paramount to know which lock point number of the bearing member is being used for the measurement in order to assess the load on the load bearing member with any equipment and temperature changes. Configuration C is accordingly connected to reference block 50 to obtain the following measurements and error corrections using lock point number s:

(15) measuring the reference block lock point frequency F3 (Hz) at lock point number s via the particular transducer 18, cable 48, couplant and P2L2 10 of configuration C;

(16) measuring the reference block temperature T3 (°F.) via thermometer 52 and cable 54;

(17) compensating F3 for temperature difference T1−T3 using Ctr by the following:

$$F3C = F3 - Ctr(T1 - T3)F1/1000000,$$

wherein F3C is the temperature compensated frequency F3; and

(18) calculating the offset compensation Fo2 by $$Fo2 = ((F1 - F3C)/F1)1000000.$$

If no compensation is made for the temperature-induced frequency change, F3 is substituted for F3C in the preceding equation. Finally, the loaded bolt at the test site is connected to configuration C and the following steps taken:

(19) measuring the bolt frequency F4 (Hz) at lock point b via the particular transducer 28, cable 48, couplant and P2L2 10 of configuration C;

(20) measuring the bolt temperature T4 (°F.) via thermometer 52 and cable 54;

(21) compensating F4 for temperature difference T2−T4 using Ct (derived in step 14) by the following:

$$F4C = F4 - Ct(T2 - T4)F2C;$$

wherein F4C is the temperature compensated frequency F4; and

(22) determining the true load:

$$load = (-1000000)Cl(((F2C - F4C)/F2C) - Fo2).$$

If no compensation is made for the temperature-induced frequency change, F2 and F4 are respectively substituted for F2C and F4C in the preceding equation. In practice, numerous bolts could be measured at one time during steps (9)−(14) using equipment configuration B to determine the respective compensated bolt reference frequencies and temperatures. Steps (1)−(4) relating to the calibration reference block 50 need only be performed once regardless of the number of bolts tested. Steps (15)−(22) are performed as desired to recertify this bolt load with the particular contemporaneous equipment configuration C and temperature T3.

As noted previously, both the lock point number s for reference block 50 and lock point number b for bearing member 20 can be determined by measuring the frequency spacing between respective successive lock points at a particular temperature and then dividing this frequency spacing into the frequency of the particular element at this temperature. The subsequent lock point frequencies are then determined by multiplying the lock point number by a subsequently measured spacing between two successive lock points.

Another method will now be described to allow one to subsequently obtain the same lock point in order to perform recertification of a load by the same equipment configuration. This method locks at the same phase point on the acoustic signal done visually using an oscilloscope and duplicating the sample/hold (S/H) setting N on the P2L2. As shown in FIGS. 5 and 7, a frequency $F_m$ defines an amplitude or resonant peak wherein $F_m = mV/2L$, wherein m is the harmonic number, and V is the velocity of the acoustic tone burst through the bearing member. The number of wavelengths λ in the bolt path is 2L/λ, wherein 2L is the round-trip or two-way length of the propagation path in the bolt. The integral number of cycles N along the reflected two-way path in the bearing member is thus equal to $2LF_m/V$, which is equal to $F_mT$, wherein T is the time required for propagation along the bolt and back. Thus, N represents a specific point in phase that is determined by the bolt length, frequency and velocity.

Figure 8A:
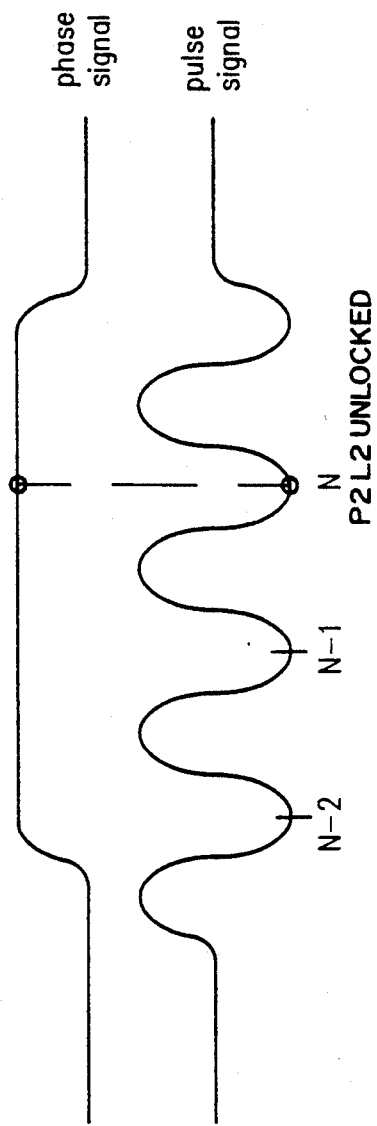
FIGS. 8a and 8b show the output of an oscilloscope at locked and unlocked positions.
Figure 8B:
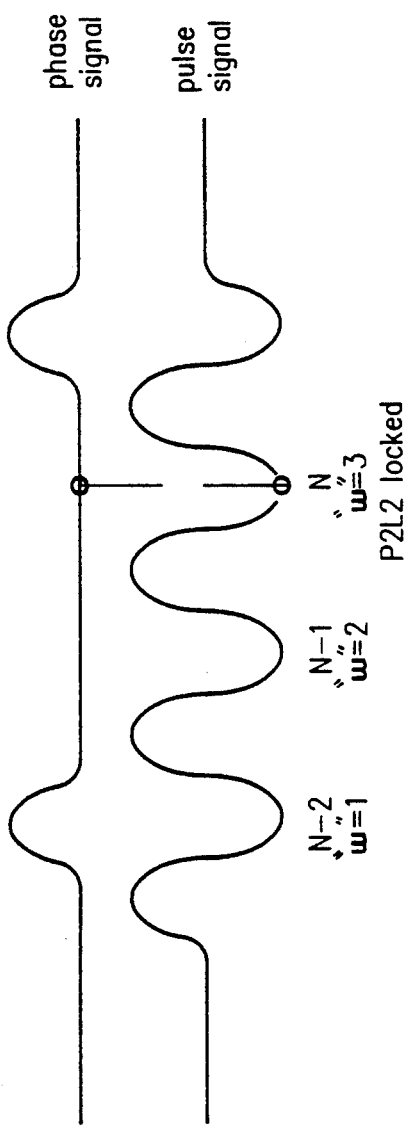

Referring to FIGS. 8a and 8b, in operation a certain P2L2 S/H setting N is selected initially for a no load condition and the wave number w in the tone burst where the S/H marker appears is noted. For example, w is the integral number of the third wave counting from left to right in FIG. 8b. The initial S/H setting N and wave number w are recorded. When the bearing member is tightened to induce a load with the P2L2 locked as shown in FIG. 8b, the frequency and the phase sample point both will shift by an amount equal to the shift in time caused by the bolt tension. If, after the bolt is loaded, the measurement system is removed from the bolt causing loss of the original P2L2 lock and then the system is reinstalled to recertify load later on, re-locking without changing any of the P2L2 setting may result in relock at a different lock point and will imply an incorrect load. To avoid any misreading, the S/H setting N on the P2L2 is duplicated and the P2L2 VCO frequency is adjusted with the P2L2 unlocked until the S/H marker is at the same wave number w on the acoustic signal as during the initial measurement. The P2L2 is then locked at the wth wave to provide a valid measurement of the frequency for determination of bolt load using this frequency for the final frequency and the particular Cl. In addition, the final temperature is measured and any temperature-induced frequency change compensated for using this temperature, the initial temperature, and a thermal calibration factor as discussed above.

In addition to duplicating the sample/hold setting, the tone burst transmission width and pulse repetition rate should also be duplicated and the measurement should be made on the same echo number (i.e., first echo=first reflection from back surface of bearing member, second echo=second reflection, etc.).

Figure 9:
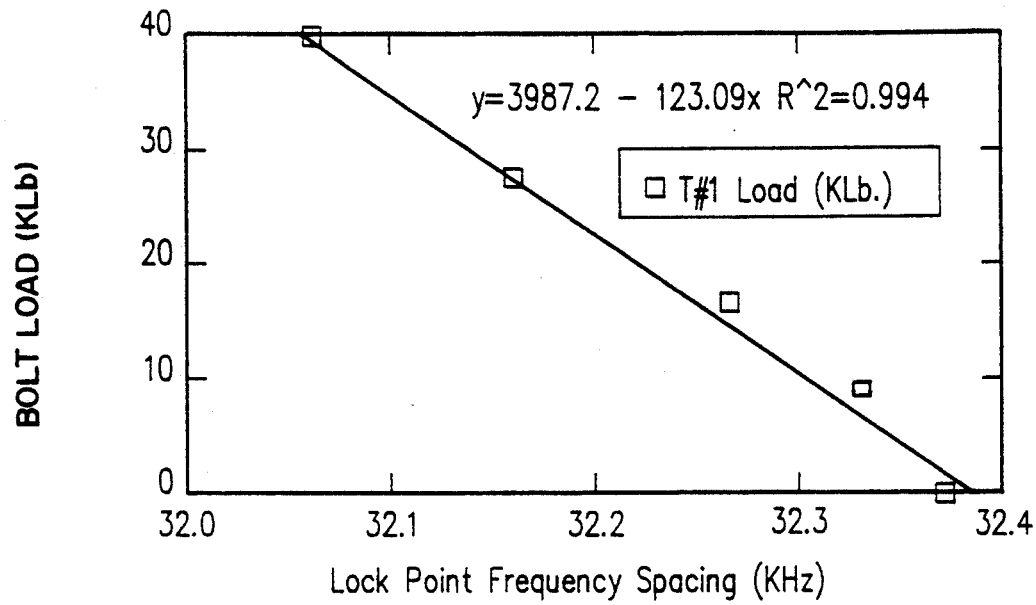
FIG. 9 is a graph showing the relationship between bolt load and lock point spacing.

An alternate approach to load recertification will now be explained. The previous two methods measure the frequency shift of one point, i.e., ΔF, to determine the load as a function of ΔF/F. This approach, on the other hand, measures the change in frequency spacing between two lock points as a function of bolt load. As illustrated in FIGS. 7 and 9, as bolt load increases the spacing between two successive lock points decreases. Lock point spacing is measured using an oscilloscope to observe the P2L2 signals by first locking to a lock point near the center of the operating frequency bandwidth of the compound resonator formed by the transducer bonded to the load bearing member by the couplant, recording this original frequency, then unlocking the P2L2, adjusting the VCO frequency until 360° (2π) of phase shift has occurred, adjusting the S/H position back to the original phase point on the ultrasonic signal, then re-locking the P2L2 and subtracting the new frequency from the original frequency to determine spacing. After loading, the above steps are repeated to determine a subsequent lock point spacing.

Referring to FIG. 9, the lock point spacing changes to a function of load. A load calibration factor Cs may be determined as discussed previously for Cl, wherein Cs is a part of a polynomial which represents an acceptable curve fit for the previously compiled load/frequency spacing data. Thus, a determination of the frequency spacing leads to a load determination.

Figure 10:
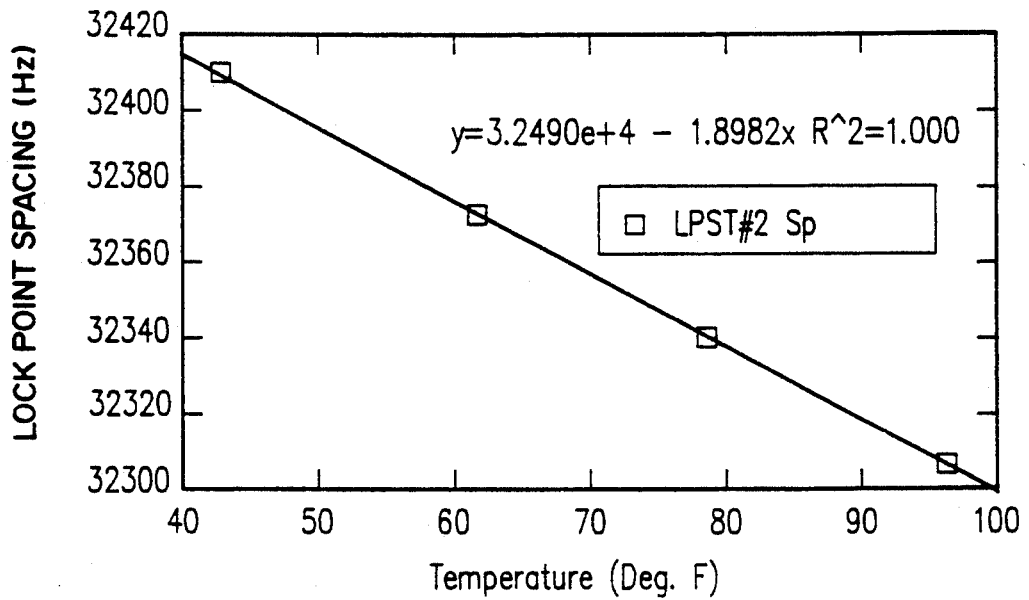
FIG. 10 is a graph showing the relationship between lock point spacing and temperature.

Referring now to FIG. 10, the lock point spacing also changes with temperature. Accordingly, a thermal calibration factor Csf is determined as discussed previously for Ct and Ctr, wherein Csf is a part of a polynomial which represents an acceptable curve fit for the previously compiled temperature/frequency spacing data. Thus, if an initial temperature reading is taken substantially contemporaneously with the original frequency spacing determination and a subsequent temperature reading is taken substantially contemporaneously with the subsequent frequency spacing determination, then a temperature compensation can be performed on the reading as discussed previously.

The determinations and calculations of the above described values can be carried out by computer 44 employing appropriate software embodying the methodologies described above.

Many modifications, improvements and substitutions will be apparent to the skilled artisan without departing from the spirit and scope of the present invention as described herein and defined in the following claims.

What is claimed is:

1. A method of recertifying a load on a bearing member using a pulsed phase locked loop (P2L2) system comprising a voltage controlled oscillator having an output frequency controlling an ultrasonic transducer coupled to the bearing member, a phase detector which compares the phase of an ultrasonic tone burst applied to the bearing member via the transducer to the phase of a tone burst reflected through the bearing member, and an adjustable sample/hold for selecting a phase point of the reflected tone burst, wherein the P2L2 system can be locked such that the phase is constant and the output frequency of the voltage controlled oscillator changes as the bearing member is loaded, the recertification method comprising the steps of:

(1) generating a first tone burst signal and a corresponding first phase signal in the bearing member in a first load condition;
   (2) adjusting the sample/hold to a determined phase point on the first phase signal;
   (3) locking the P2L2 on the first phase signal at the sample/hold phase point to determine a first load measurement;
   (4) correlating the sample/hold phase point with a corresponding position w on the first tone burst signal;
   (5) generating a second tone burst signal and a corresponding second phase signal in the bearing member in a second load condition;
   (6) adjusting the sample/hold setting to the same sample/hold phase point of step (3);
   (7) adjusting the output frequency of the voltage controlled oscillator until the sample/hold is positioned at the previously determined phase point corresponding to position w on the second tone burst signal; and
   (8) locking the P2L2 at this phase point corresponding to position w on the second tone burst signal to determine a frequency of the tone burst which is indicative of the second loading condition.

2. The method according to claim 1, further comprising the steps of:

(9) measuring the temperature of the bearing member substantially contemporaneously with step (3);
   (10) measuring the temperature of the bearing member substantially contemporaneously with step (8); and
   (11) compensating for any temperature induced change in the frequency using a predetermined thermal correction factor and the difference between the temperatures measured in steps (9) and (10).

* * * * *